United States Patent
Dmitrovic et al.

(10) Patent No.: US 6,321,747 B1
(45) Date of Patent: Nov. 27, 2001

(54) INHALATION DEVICE

(75) Inventors: Bosko Dmitrovic, Evreux Cedex (FR); Paul Kenneth Rand, Hertfordshire; Peter John Brand, Herfordshire, both of (GB); Etienne Seguelas, Chateau-Landon; David Buday-Goldberger, Rion, both of (FR)

(73) Assignee: SmithKline Beecham Corporation, Research Triangle Park, NC (US)

( * ) Notice: Subject to any disclaimer, the term of this patent is extended or adjusted under 35 U.S.C. 154(b) by 0 days.

(21) Appl. No.: 09/341,221

(22) PCT Filed: Jan. 6, 1998

(86) PCT No.: PCT/EP98/00023

§ 371 Date: Nov. 19, 1999

§ 102(e) Date: Nov. 19, 1999

(87) PCT Pub. No.: WO98/30262

PCT Pub. Date: Jul. 16, 1998

(30) Foreign Application Priority Data

Jan. 8, 1997 (GB) .................................................. 9700226

(51) Int. Cl.[7] .......................... A61M 15/00; A61M 16/00; B05D 7/14; B65D 83/06
(52) U.S. Cl. ................................ 128/203.15; 128/203.19; 222/499
(58) Field of Search ........................ 128/203.12, 203.15, 128/203.19–203.24, 203.28; 215/222, 225; 222/498, 499

(56) References Cited

U.S. PATENT DOCUMENTS

| 3,662,915 | | 5/1972 | Destler, Jr. . |
| 4,762,248 | | 8/1988 | Uhlig . |
| 5,331,953 | * | 7/1994 | Andersson et al. ............. 128/200.14 |
| 5,394,868 | * | 3/1995 | Ambrosio et al. .............. 128/203.15 |
| 5,421,482 | * | 6/1995 | Garby et al. ............................ 222/36 |
| 5,524,613 | | 6/1996 | Haber et al. . |
| 5,611,444 | * | 3/1997 | Garby et al. .......................... 215/230 |
| 5,687,710 | * | 11/1997 | Ambrosio et al. .............. 128/203.15 |
| 5,718,355 | * | 2/1998 | Garby et al. ............................ 222/36 |
| 5,740,792 | * | 4/1998 | Ashley et al. ................... 128/203.15 |
| 5,799,651 | * | 9/1998 | Garby et al. .................... 128/200.23 |
| 5,829,434 | * | 11/1998 | Ambrosio et al. .............. 128/203.15 |
| 6,065,471 | * | 5/2000 | Schaeffer et al. ............... 128/203.15 |

FOREIGN PATENT DOCUMENTS

| FR 1 587 657 A | 3/1970 | (FR) . |
| WO94 11044 A | 5/1994 | (WO) . |
| WO96 08284 A | 3/1996 | (WO) . |

* cited by examiner

Primary Examiner—John G. Weiss
Assistant Examiner—Joseph F. Weiss, Jr.
(74) Attorney, Agent, or Firm—James P. Riek

(57) ABSTRACT

Inhalation device comprising a body (55) defining a reservoir (56) for medicament in the form of a powder, an outlet (57) through which a user can inhale, and a dosing member (53) with at least one metering recess formed therein. The dosing member (53) is moveable between a first position in which the at least one metering recess communicates with the reservoir (56) to receive a dose of powder therefrom and a second position in which the at least one metering recess communicates with the outlet (57) to permit the user to inhale the dose. The at least one metering recess is formed in a face of the dosing member which is urged into contact against a similar mating face of the body at the lower end of the reservoir to form a dynamic seal. At least one of the faces (51) is made of a flexible material having a hardness of less than 80 Shore A.

10 Claims, 7 Drawing Sheets

INHALATION DEVICE

This application is filed pursuant to 35 U.S.C. §371 as a United States National Phase Application of International Application No. PCT/EP98/00023 filed Jan. 6, 1998, which claims priority from GB 9700226.5 filed Jan. 8, 1997.

This invention relates to an inhalation device by means of which metered doses of medicament in the form of a powder can be dispersed to a user. In particular it relates to a device of the type in which the medicament powder is held in bulk in a reservoir with which the device is provided, and is metered to the user from the reservoir.

International Patent Application Publication No. WO 96/08284 describes an inhalation device of the type just described, comprising a body defining a reservoir for medicaments in powder form, an outlet through which a user can inhale and a dosing member with at least one metering recess formed therein. The dosing member is moveable between a first position in which the metering recess communicates with the reservoir to receive a dose of powder therefrom and a second position in which the metering recess communicates with the outlet to permit the user to inhale the dose. The metering recess is formed in a smooth flat face of the dosing member which is mounted in contact against a similar flat face of the body at the lower end of the reservoir. The contacting flat faces are made of a hard material having highly polished smooth surfaces which form an effective dynamic seal between the dosing member and body to prevent both loss of powder from and ingression of moisture into the reservoir through the interface between the base and dosing member.

In order to provide the desired sealing characteristics both contacting surfaces must be lapped and polished to ensure very closely matching contours and a high degree of smoothness. Any slight undulation of contour or roughness of finish in either of the contacting surfaces would impair the sealing characteristics. Thus, the precision of finish required on these surfaces demands accurate lapping and polishing operations which add considerably to manufacturing costs.

It is an object to provide a device of the type just described employing an effective dynamic seal which is cheaper and easier to produce.

According to the present invention there is provided an inhalation device comprising a body defining a reservoir for medicament in the form of a powder, an outlet through which a user can inhale, and a dosing member with at least one metering recess formed therein, the dosing member being moveable between a first position in which the at least one metering recess communicates with the reservoir to receive a dose of powder therefrom and a second position in which the at least one metering recess communicates with the outlet to permit the user to inhale the dose, the at least one metering recess being formed in a face of the dosing member, the face being urged into contact against a similar mating face of the body at the lower end of the reservoir to form a dynamic seal, characterised in that at least one of the faces is made of a flexible material having a hardness of less than 80 Shore A. The term 'dynamic seal' in this context means a seal that allows and can withstand relative movement of the two faces.

By having at least one of the sealing faces made of a flexible material it is not necessary for either of the faces to have a precision finish to ensure very closely matching contours since the flexible material will compensate for any undulations to maintain an effective seal.

Preferably the flexible material has a coefficient of friction of 0.4 or less. By use of a material having a low coefficient of friction the faces will move smoothly and easily over each other so aiding smooth operation of the device.

Suitably the faces are flat.

Suitably the mating face of the body is made of a flexible material. Preferably the mating face of the body comprises a rubber insert. Suitably, the rubber insert has a hardness between 40 and 60 Shore A.

Preferably the rubber insert comprises chlorinated butyl or butyl laminated with a contacting face made of a layer of PTFE, polypropylene or polyethylene.

Suitably the face of the dosing member is of unitary construction with the dosing member.

The invention is further described below with reference to the accompanying drawings in which.

Figure 1:
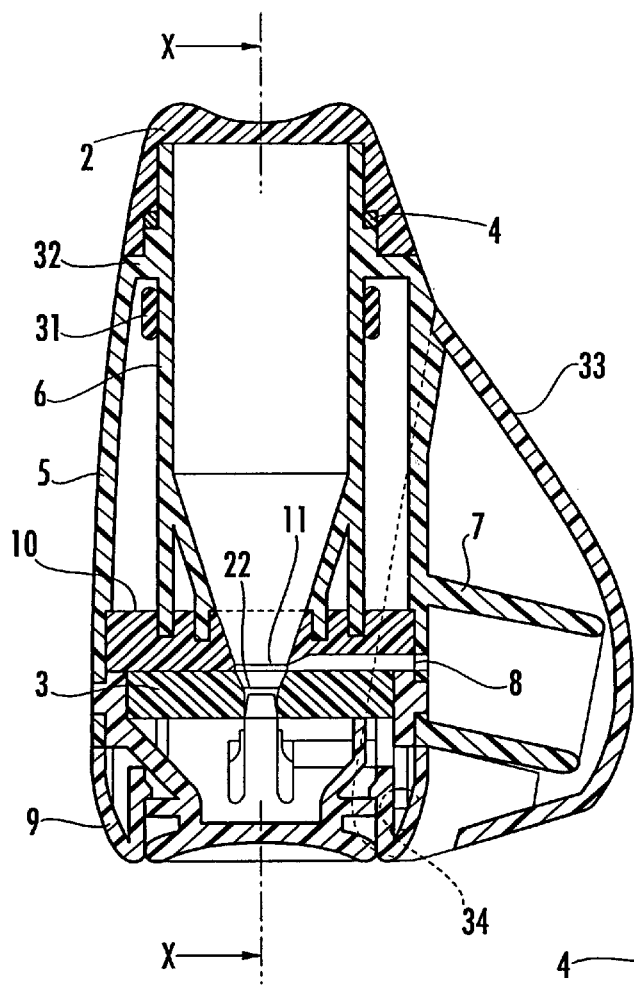
FIG. 1 is a section through a device according to the invention.
Figure 2:
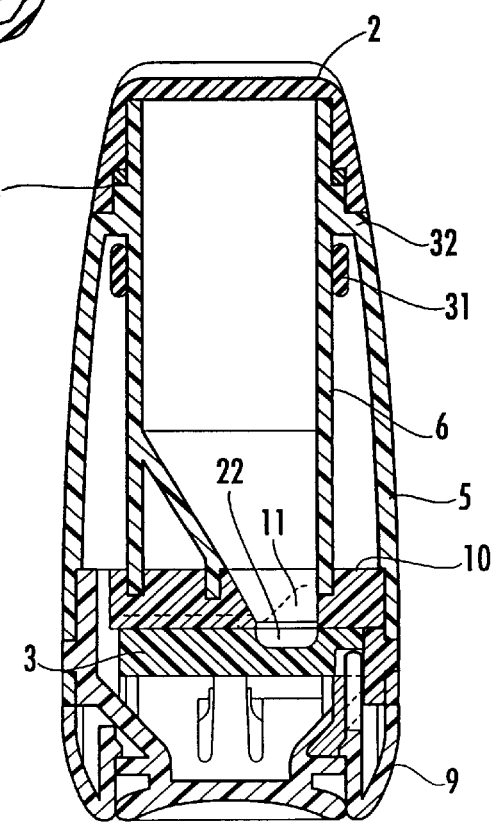
FIG. 2 is a section on line X—X in FIG. 1.

The device shown in cross section in FIGS. 1 and 2 comprises a main body portion 5 which defines a reservoir 6 and a reservoir cover or end cap 2. The reservoir 6 contains a supply of medicament in the form of a powder (not shown). The medicament is one which is suitable for inhalation, and many such medicaments are well known to those skilled in the art, for example for the treatment of asthma. Powdered medicaments suitable for this purpose include salbutamol, beclomethasone, satmeterol, fluticasone, formoterol, terbutaline, budesonide and flunisolide, and physiologically acceptable salts, solvates and esters or any combination thereof. Preferred medicaments are salbutamol, salbutamol sulphate, salmeterol, salmeterol xinafoate, fluticasone propionate, beclomethasone dipropionate and terbutaline sulphate. Individual isomers, such as R-salbutamol, can also be used. It is to be understood that the medicament powder may consist purely of one or more active ingredients, or there may additionally be a carrier, for example lactose powder.

The reservoir cover 2 may be provided with a desiccant cartridge (not shown) to absorb moisture and reduce the risk of the powder in the reservoir absorbing moisture and undergoing agglomeration of the particles thereof. The cover 2 may be removably secured to the body 5 by any known means, for example by means of a screw thread or a snap fit, to enable refilling of the reservoir 6 with powder. Alternatively, the device may be intended to be disposable after exhaustion of the supply of powder in the reservoir, in which case the cover 2 may be permanently secured to the body 5 by means of an interference fit or by use of an adhesive, ultrasonic welding or any other method, such as that described below with reference to FIGS. 10 and 11. A pharmaceutical grade rubber sealing ring 4 may be incorporated between the cover 2 and body 5 to prevent ingression of moisture into the reservoir 6.

At its lower end the main body portion 5 is fitted with a base 10 which together with body 5 defines an aperture 11 which is offset from the vertical axis of the device and through which powder can pass from the reservoir to the dosing member 3. Powder is guided to the aperture by the walls of the reservoir which form a hopper. Extending laterally from the lower end of main body 5 is mouthpiece 7. If, however, the device were intended for nasal inhalation this would be replaced by a nosepiece. Dosing member 3 having a metering recess 22 is mounted upon lower body portion 9 which is pivotally connected to main body 5 such that it may rotate about the vertical axis of the device. As explained in more detail below, lower body portion 9 serves to allow rotation of the dosing member 3 whilst maintaining the same in axial alignment with base 10. It also urges the dosing member 3 into close contact with base 10. Dust cover 33 is attached to lower body portion 9 through pivot 34.

A weight 31 in the form of a ring encircles the reservoir 6 and is slidable longitudinally thereof. The locus of movement of the weight 31 is defined towards the top of the reservoir by an end stop 32 formed as an integral part of the body 5, and towards the bottom of the reservoir by base 10 which behaves as an anvil. It is to be understood that whilst the device described herein incorporates a weight for the purpose described below, the weight is not an essential element of the invention and it might be chosen to omit the incorporation of the weight.

The lower face of the base 10 is formed by a flat flexible rubber insert (not shown), while the upper face of dosing member 3 is moulded with a flat contacting face to form a dynamic seal between the body and dosing member. These flat faces provide contacting surfaces between which there is substantially no clearance. Air and powder are thus excluded from the interface between the base 10 and dosing member 3 both in the static state and during the sliding motion of one face over the other minimising both loss of powder from and ingression of moisture into the reservoir 6 through the interface between the base 10 and dosing member 3. This type of dynamic or sliding seal obviates the need for any additional sealing means between base 10 and dosing member 3.

The contacting faces need not be provided with precision finishes to provide an effective seal. Any undulations in the flatness of the upper face of the dosing member will be compensated for by the flexible rubber insert to maintain an effective seal. Although adequate performance of the seal may be achieved using a rubber material having a hardness of below 80 Shore A, it has been found that optimal performance of the seal is achieved using a rubber material having a hardness of between 40 and 60, Shore A. If the hardness of the rubber is below 40 Shore A, the rubber insert tends to deform into metering recess 22, so scraping powder out of the recess and reducing the quantity of powder metered. On the other hand, if the hardness of the rubber is above 60 Shore A, the effectiveness of the seal may be impaired. Smooth finishes on both contacting faces are desirable to maintain a good seal, but good results have been obtained from contacting faces moulded directly from highly polished tooling with no additional manufacturing process.

The rubber insert may be made from butyl to provide the desired hardness and flexibility. However, butyl has a high coefficient of friction and tends to hinder movement of the contacting faces relative to each other. It is therefore preferable to use either chlorinated butyl or butyl laminated with a contacting face made of a layer of PTFE, polypropylene or polyethylene. Such rubber inserts may be manufactured by standard techniques and provide a contact face with reduced coefficient of friction. Alternatively, the contacting face may be subject to any other surface treatment that reduces friction, such as plasma modification or varnish.

PTFE is a particularly suitable material for this purpose due to its low coefficient of friction (below 0.1), though materials having coefficients of friction up to around 0.4 may be acceptable. Good results have been achieved using butyl laminated with a contacting face made of PTFE foil having a thickness of around 0.2 mm. The foil may be adhered to the rubber insert without glue using standard manufacturing techniques. If the PTFE foil is thinner than 0.2 mm, the foil tends to crumple during vulcanisation of the rubber, while if the foil is thicker than 0.2 mm, the insert becomes harder and the effectiveness of the seal may be impaired.

The contacting face of the dosing member may be integrally moulded with the dosing member of any suitable material, e.g. acetal resin. Alternatively, it will be understood that the contacting face of the dosing member may be formed by a flat flexible rubber insert as described above and lower face of base 10 may be integrally moulded in one piece as part of base 10 from a suitable material. Alternatively, both faces may be formed by flat flexible rubber inserts as described.

In the embodiment described, the two faces are formed by the surfaces of flat discs. It will be appreciated that disc shapes are not essential. Contact faces may be formed by the surfaces of a frusto-cone and a correspondingly frusto conical socket, by the contacting surfaces of two co-axial cylinders or by two correspondingly partially spherical contacting ball and socket surfaces.

Figure 3:
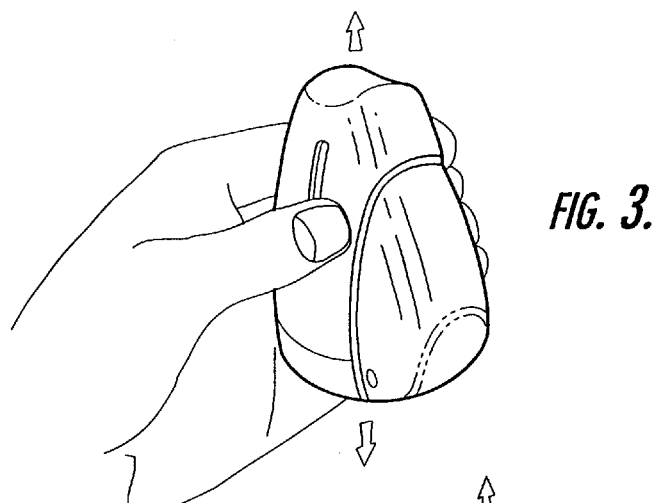
FIGS. 3 to 5 are perspective views showing three steps in the operation of the device according to FIGS. 1, 2 and 6 to 9.

In operation, the user initially shakes the device in a generally upward and downward motion while maintaining the device in a generally upright orientation as shown in FIG. 3. Weight 31 is thereby caused to travel up and down the reservoir, so repeatedly striking end stop 32 and base 10. The jolts which this produces causes the powder in the reservoir to be urged downwardly and to enter the metering recess 22.

Figure 4:
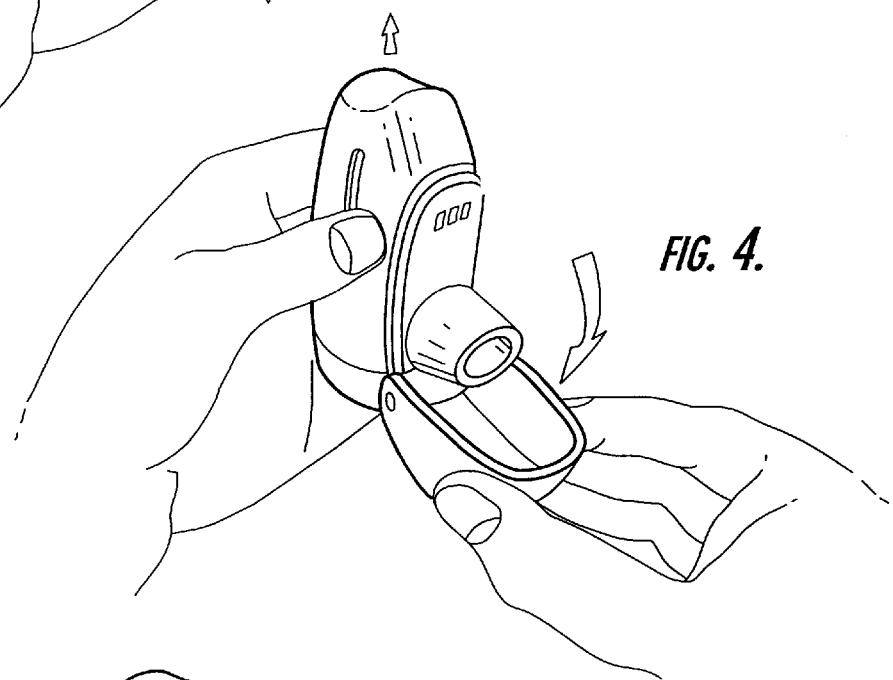
Figure 5:
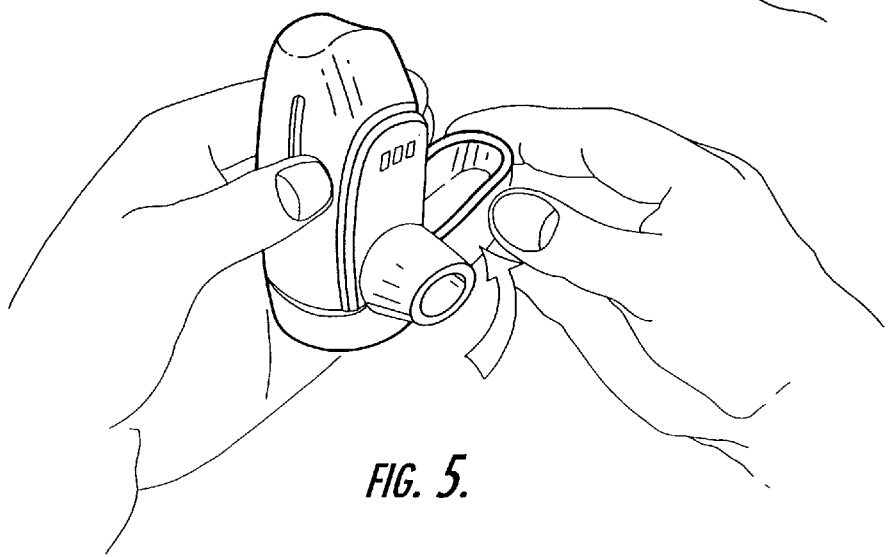

The user then opens dust cover 33, as shown in FIG. 4, and rotates the cover which is connected to lower body portion 9 as described above and shown in FIG. 5, to move the dust cover 33 away from the mouthpiece 7 to allow access thereto and to bring the recess 22 into alignment with the aperture 8 leading to the mouthpiece 7. The user knows when this position has been reached as the lower body portion 9 engages a stop (not shown) and will not move any further. The user then inhales through mouthpiece 7. After inhalation the user returns the lower body portion 9 to its initial position and closes the dust cover 33.

In the device shown in FIGS. 1 and 2 the aperture 11 is radially offset by an angle of 90° about the vertical axis of the device from the aperture 8 at the inner end of the mouthpiece to allow the dust cover and lower body portion 9 to be moved through 90° for ease of access to the mouthpiece. However, it will be appreciated that this angle can be substantially increased or slightly decreased according to the desired angle of rotation of the dust cover, lower body portion and dosing member.

Further possible modifications to the device described include incorporation of a suitable dose counting mechanism to give the user an indication of the amount of powder remaining in the device.

A further embodiment of the invention is shown in FIGS. 6 to 9. As in the previous embodiments, the device shown in cross section in FIGS. 6 and 7 and in exploded view in FIG. 8 comprises an elongate main body portion 55 which defines a reservoir 56 and a reservoir cover or end cap 52. The reservoir 56 contains a supply of medicament in the form of a powder (not shown). The reservoir cover 52 is secured to the body 55 by a snap fit and a pharmaceutical grade rubber sealing ring 54 is incorporated between the cover 52 and body 55 to prevent ingression of moisture into the reservoir 56.

Figure 6:
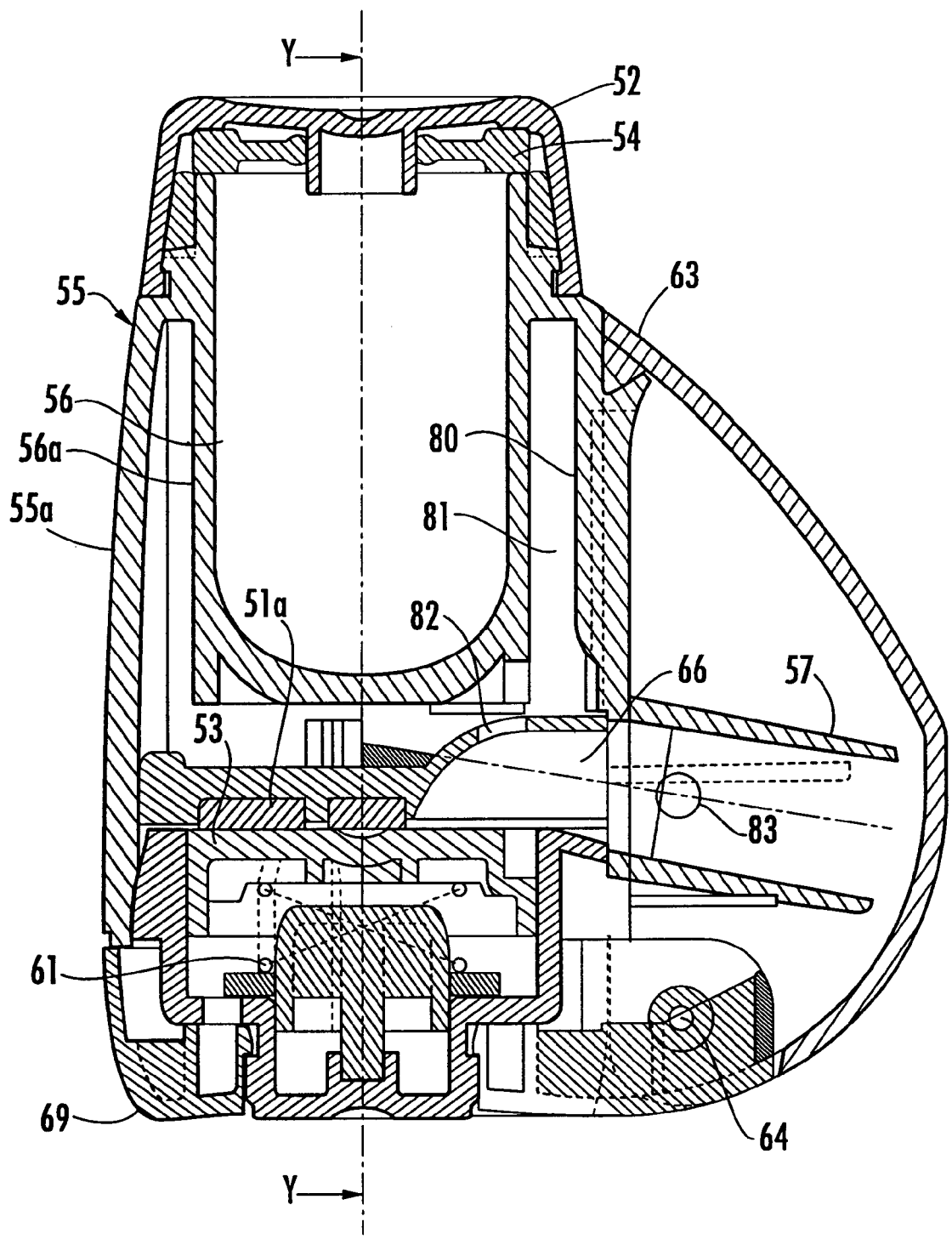
FIG. 6 is a section through a second embodiment of a device according to the invention.
Figure 7:
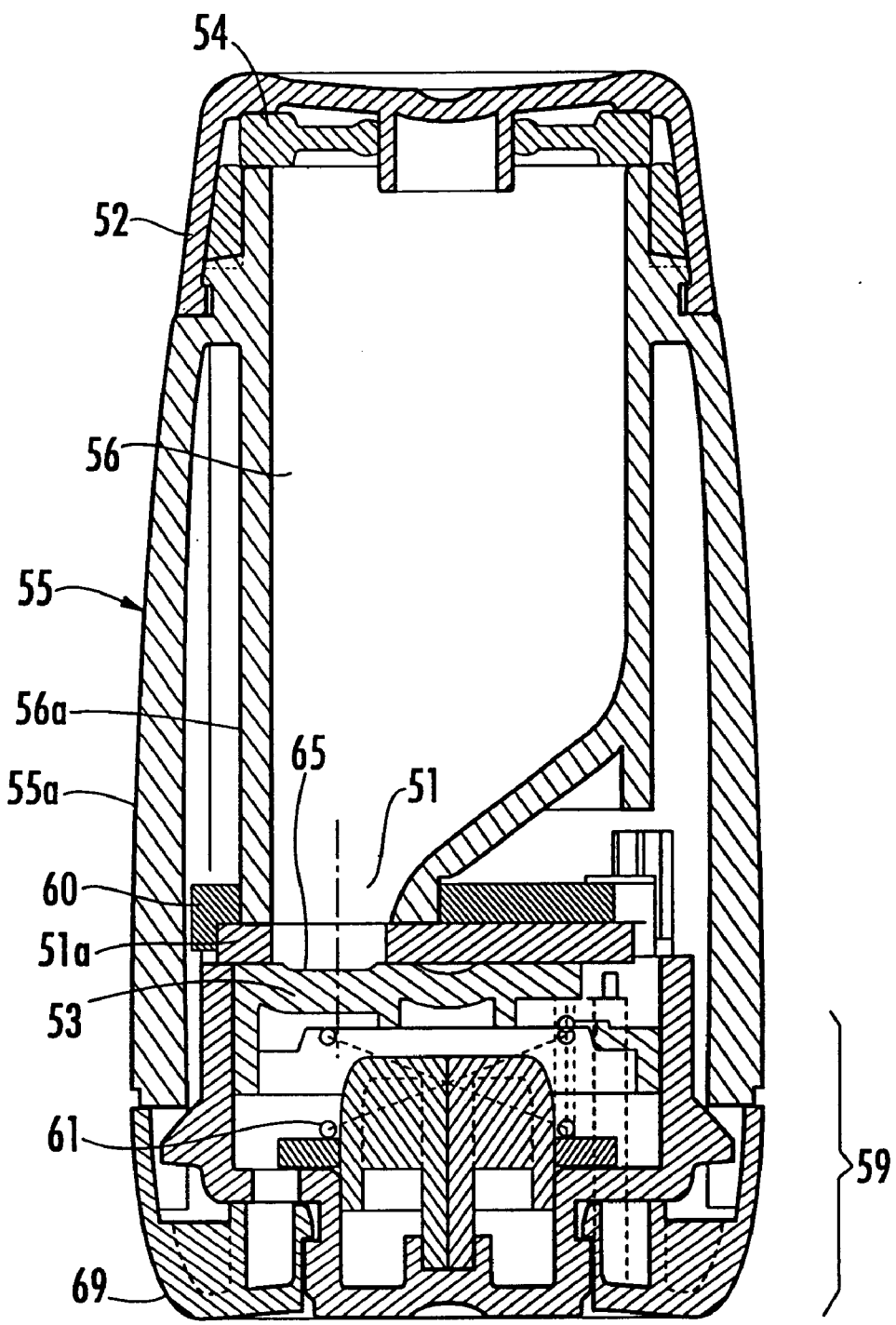
FIG. 7 is a section on line Y—Y in FIG. 6.
Figure 8:
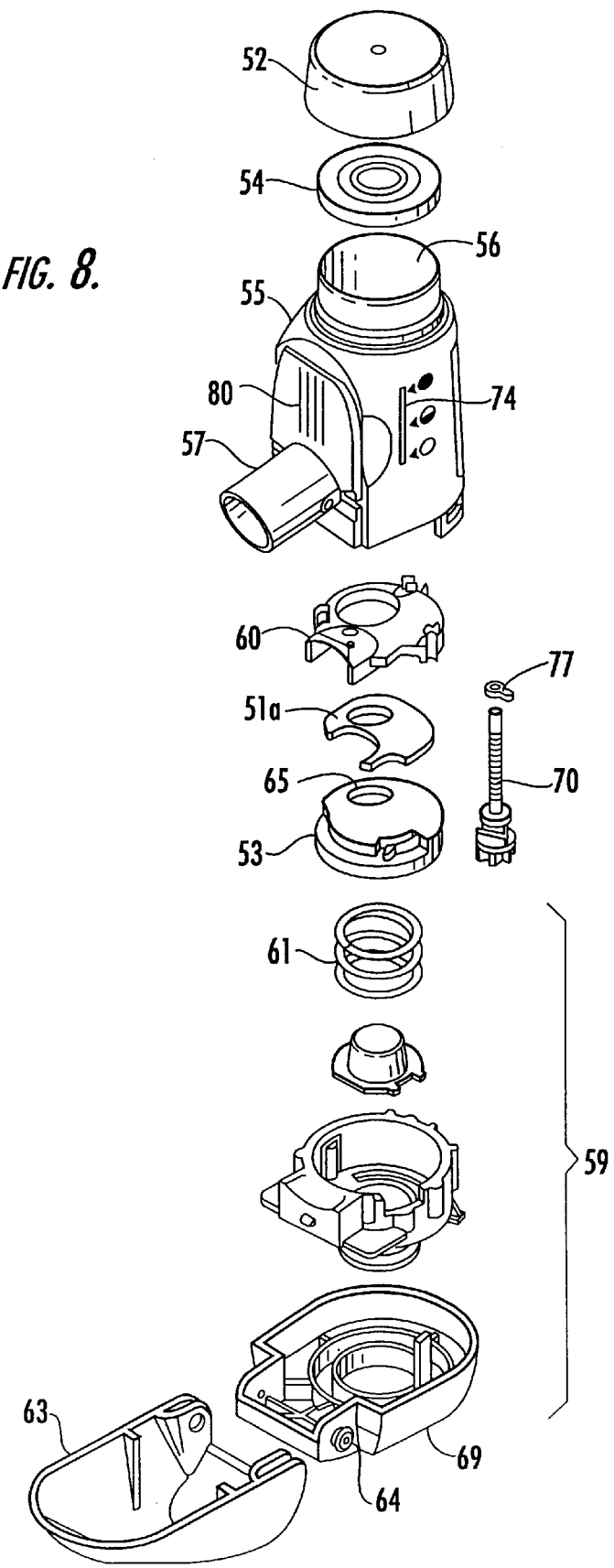
FIG. 8 is an exploded view of the embodiment shown in FIGS. 6 and 7.

As best shown in FIGS. 7 and 8, a base member 60, possessing an opening, is fitted to the lower end of reservoir 56. A flat flexible rubber insert 51a is provided at the lower face of base member 60. Insert 51a abuts a portion of the lower end of reservoir 56 extending through the opening in base member 60. A dosing member 53, defining a recess 65 and possessing an upper face with a flat contact surface, is positioned at the lower surface of rubber insert 51a. The dosing member 53 is mounted upon lower body assembly 59 which is pivotally connected to main body 55 by engaging the housing wall 55a such that it may rotate about the vertical axis of the device. As can be seen in FIGS. 6–8, lower body assembly 59 serves to transmit rotational movement thereof to the dosing member 53 whilst maintaining the same in axial alignment with base member 60. It also urges dosing member 53 into close contact with base member 60 by means of a spring 61. Dust cover 63 is attached to lower body portion 69 through pivot 64. A mouthpiece 57 extends laterally from a lower end of the main body 55.

The lower end of the reservoir 56 and the insert 51a define an aperture 51, which is offset from the vertical axis of the device. The powder contained within reservoir 56 is guided to aperture 51 by the walls of the reservoir 56a, which form a hopper. When the recess 65 of dosing member 53 is rotationally aligned with the aperture 51, powder can pass from the reservoir 56 to the dosing recess 65.

Figure 9:
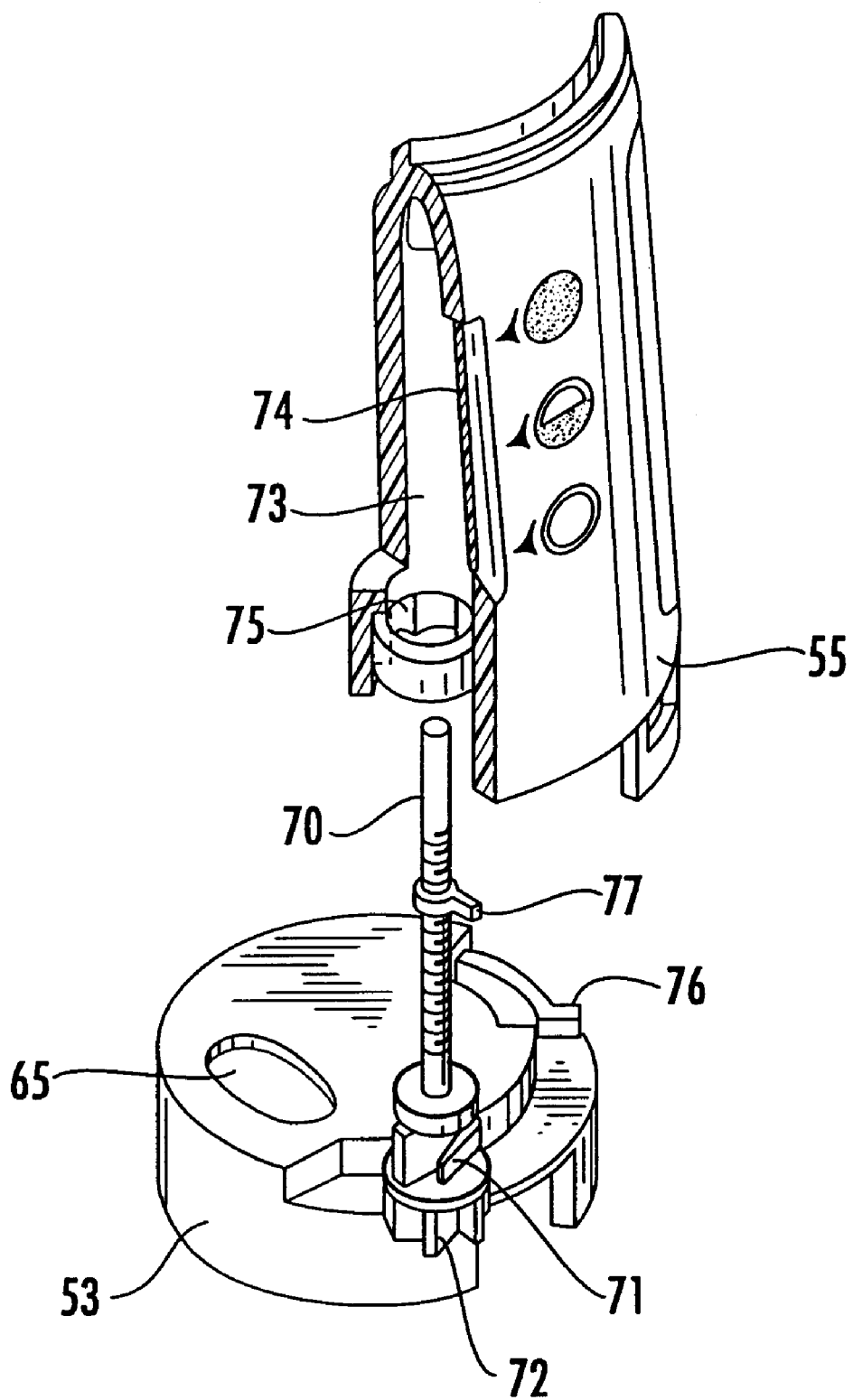
FIG. 9 is an exploded perspective view, partly cut away, showing the dose indicator mechanism of the embodiment shown in FIGS. 6 to 8.

A dose indicator drive means comprising a shaft 70 provided with a screw thread over much of its length, a sprung lug 71 at the base of the thread and a sprocket 72 with inclined teeth positioned below the lug is rotatably mounted within a bore 73 in the wall of the main body 55 (see FIG. 9). An indicator nut 77 is threaded onto the shaft with a projection protruding through an indicator window 74 in the wall of bore 73 which prevents the indicator nut 77 from rotating with shaft 70. Sprung lug 71 engages with teeth 75 formed within bore 73 to form a ratchet allowing shaft 70 to rotate in one direction only. Sprocket 72 is located adjacent the periphery of dosing member 53 which is provided with a second sprung lug 76.

Operation of the device is similar to that described with reference to the embodiment shown in FIGS. 1 to 5. The user initially shakes the device in a generally upward and downward motion while maintaining the device in a generally upright orientation as shown in FIG. 3. This encourages powder to flow downwardly and enter metering recess 65 within dosing member 53.

The user then opens dust cover 63, as shown in FIG. 4, and rotates the cover which is connected to lower body assembly 59 as described above and as shown in FIG. 5, to move dust cover 63 away from mouthpiece 57 to allow access thereto and to bring recess 65 into alignment with the aperture at 66 leading to the mouthpiece 57. As the dosing member 53 rotates with the lower body assembly 59, lug 76 (FIG. 9) engages an inclined tooth presented by sprocket 72 of the dose indicator drive means. The dose indicator drive means is prevented from turning in the direction urged by lug 76 by virtue of the ratchet mechanism formed by teeth 75 and lug 71. As a result, lug 76 rides over the inclined tooth and out of engagement with sprocket 72. The lower body assembly 59 engages a stop (not shown) and will not move any further when the recess 65 is correctly aligned with aperture 66.

The user now inhales through mouthpiece 57. Air is drawn through grill 80 and passage 81, defined by body 55 and hole 82 in base member 60, and entrains the powder in recess 65 of dosing member 53. The airflow draws the entrained powder through the mouthpiece 57 and is inhaled by the user. Further air is drawn into the mouthpiece through holes 83 on either side of mouthpiece 57 and this creates turbulence which helps to break-up any agglomerates of powder entrained.

After inhalation the user returns lower body assembly 59 to its initial position and closes the dust cover 63. As dosing member 53 rotates, lug 76 again engages sprocket 72 of the dose indicator drive means. As the ratchet mechanism formed by teeth 75 and lug 71 allows movement of the dose indicator drive means in the direction as now urged by lug 76, the dose indicator drive means is rotated by one tooth pitch through engagement with lug 76 as it passes sprocket 72. Rotation of the dose indicator drive means causes the captive dose indicator nut 73 to travel down threaded shaft 70. The pitch of the thread and the number of teeth on sprocket 72 are selected to ensure that the dose indicator nut travels from the uppermost "full" position to the lowermost "empty" position when the device has been used sufficiently to deliver its prescribed number of doses, so indicating to the user that the device is empty.

Figures 10, 11:
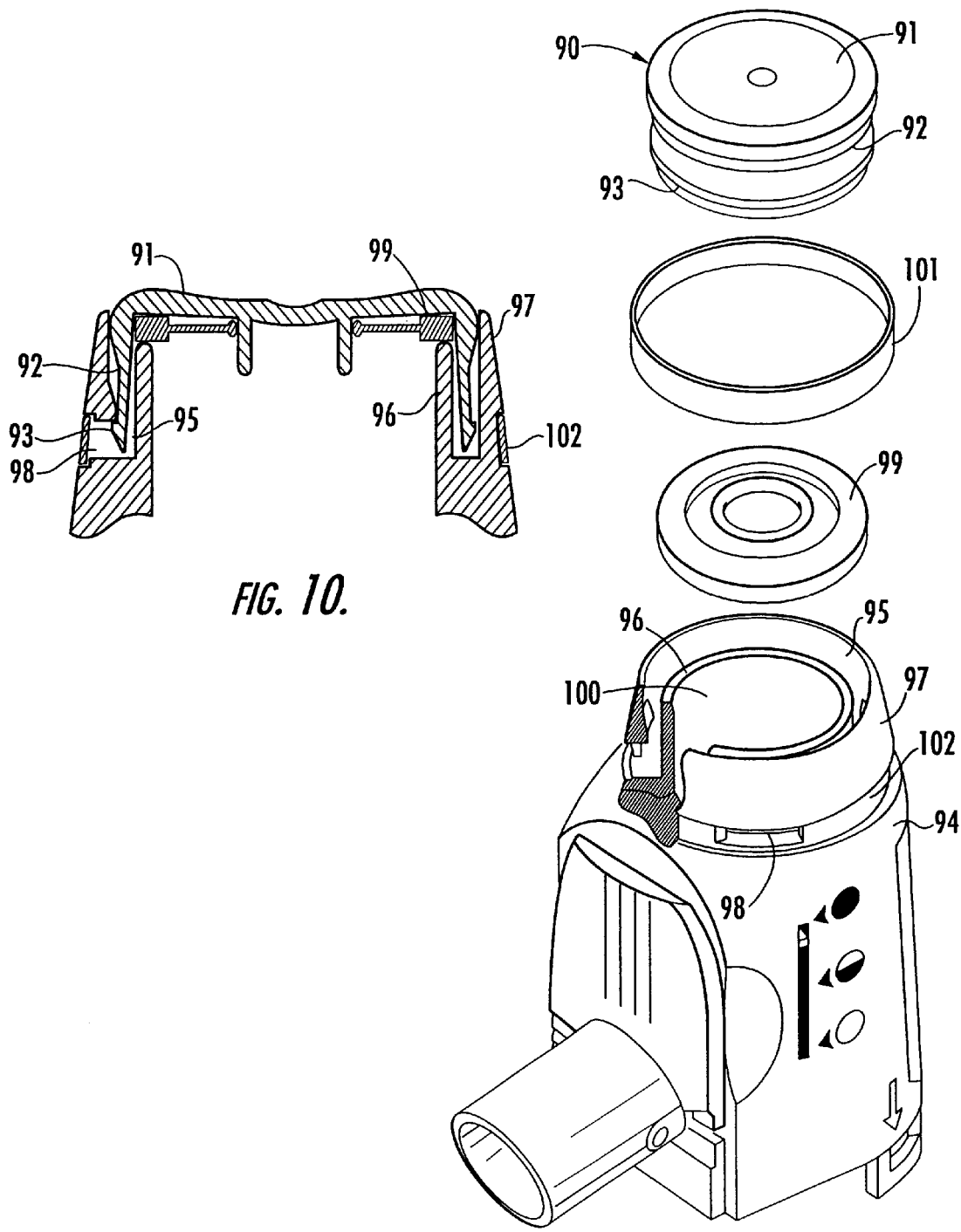
FIG. 10 is a section through a tamper resistant reservoir cover assembly for use with a device according to the invention.
FIG. 11 is an exploded and partially sectioned view through the reservoir cover assembly shown in FIG. 10.

FIGS. 10 and 11 show an alternative design for a tamper resistant reservoir cover assembly which may be used with a device according to the invention or for other applications where it is desired to seal a container to prevent access to its contents. The cover assembly comprises a cap 90 which has a circular top portion 91 and an annular depending cylindrical portion 92 formed with an outwardly directed protrusion or lip 93 extending around its lower periphery. The cap 90 is made of a material such as polypropylene which allows some resilient flexibility of the cylindrical portion 92, the purpose of which is explained below.

The top of the body 94 is formed with an outer peripheral wall 97 and a concentric inner peripheral wall 96 which together define the mouth of the reservoir 100. An annular channel 95 is further defined between inner and outer peripheral walls 96, 97. The outer wall 97 has an increased wall thickness extending into channel 95 at distinct locations around its inner face which forms retaining ledges under which lip 93 latches, as seen in FIG. 10. For manufacturing purposes, the ledges are formed by means of five equispaced slots 98 extending radially through to channel 95 from a groove 102, which is provided around the periphery of outer wall 97 at the same level as the bottom of channel 95. The inner surface of the outer wall forms an inclined slope leading from the upper part of channel 95 to the point of maximum wall thickness just above each slot 98.

To fit cap 90 to body 94, the cylindrical portion 92 is inserted into channel 95. As the lower periphery of the cylindrical portion 92 contacts the inclined slopes formed on the outer wall 97, the cap 90 is pushed down onto the body 94 such that the cylindrical portion 92 flexes inwardly due to its resilient flexibility at the regions of contact to allow further movement into channel 95, until lips 93 reach slots 98 and snap outwardly to latch under the retaining ledges. When assembled, cylindrical portion 92 is substantially surrounded by outer peripheral wall 97 such that it is concealed and inaccessible from the outside. Sealing ring 99 is sandwiched between the top of inner wall 96 and the underside of top portion 91 to seal the reservoir 100 from the atmosphere. Finally, band 101 of polypropylene or copolymere polypropylene-polyethylene is stretched around groove 102 to hide slots 98 and to prevent access and tampering with lips 93. Once in place, band 101 is not easily removed.

It will be understood that the present disclosure is for the purpose of illustration only and the invention extends to modifications, variations and improvements thereto.

What is claimed is:

1. Inhalation device comprising a body defining a reservoir for medicament in the form of a powder, an outlet through which a user can inhale, and a dosing member with at least one metering recess formed therein, the dosing member being moveable between a first position in which the at least one metering recess communicates with the reservoir to receive a dose of powder therefrom and a second position in which the at least one metering recess communicates with the outlet to permit the user to inhale the dose, the at least one metering recess being formed in a face of the dosing member, the face being urged into contact against a similar mating face of the body at the lower end of the reservoir to form a dynamic seal, characterised in that at least one of the faces is made of a flexible material having a hardness of less than 80 Shore A.

2. Inhalation device according to claim 1, characterised in that the flexible material has a coefficient of friction of 0.4 or less.

3. Inhalation device according to claim 1, characterised in that the faces are flat.

4. Inhalation device according to claim 1, characterised in that the mating face of the body is made of a flexible material.

5. Inhalation device according to claim 4, characterised in that the mating face of the body comprises a rubber insert having a hardness of between 40 and 60 'Shore A.

6. Inhalation device according to claim 5, characterised in that the rubber insert comprises chlorinated butyl or butyl laminated with a contacting face made of a layer of PTFE, polypropylene or polyethylene.

7. Inhalation device according to claim 1, characterised in that the face of the dosing member is of unitary construction with the dosing member.

8. The inhalation device of claim 1, further comprising a tamper resistant closure closing an opening in the body, the body defining an outer peripheral wall adjacent the opening and presenting at least one inner ledge below the opening, the closure comprising a cylindrical skirt portion having a lip on its outer periphery, whereby when assembled the lip forms a snap fit with the ledge to hold the closure in place.

9. The inhalation device of claim 8, wherein the body further defines an inner peripheral wall which seals against the closure when assembled.

10. The inhalation device of claim 8, wherein the outer peripheral wall of the body, when assembled with the tamper resistant closure, conceals the skirt portion such that the skirt portion is substantially inaccessible from outside.

* * * * *